(12) United States Patent
Serrano et al.

(10) Patent No.: US 7,748,248 B2
(45) Date of Patent: Jul. 6, 2010

(54) STENT CRIMPING MECHANISMS

(75) Inventors: Gabriel Sorbrino Serrano, Kinvara (IE); David McMorrow, Galway (IE); Dennis Aamoth, Fridley, MN (US); Bruce Asmus, Minnetonka, MN (US); Thomas Walch, Centerville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1505 days.

(21) Appl. No.: 11/087,411

(22) Filed: Mar. 23, 2005

(65) Prior Publication Data
US 2006/0213049 A1  Sep. 28, 2006

(51) Int. Cl.
*B21J 7/00* (2006.01)
*B21D 41/04* (2006.01)

(52) U.S. Cl. ............... 72/402; 72/396; 72/416

(58) Field of Classification Search .......... 72/402, 72/396, 399, 431, 434, 465.1, 466.8, 466.9, 72/416, 432, 466.7, 453.01
See application file for complete search history.

(56) References Cited

U.S. PATENT DOCUMENTS

| | | | | |
|---|---|---|---|---|
| 3,924,440 A * | 12/1975 | Vinje | ............... | 72/397 |
| 4,578,983 A * | 4/1986 | Kimura | ............... | 72/407 |
| 6,387,117 B1 | 5/2002 | Leanna et al. | ............... | 623/1.1 |
| 6,618,921 B1 | 9/2003 | Thornton | ............... | 29/270 |
| 6,769,161 B2 | 8/2004 | Klisch et al. | ............... | 29/234 |
| 6,783,542 B2 | 8/2004 | Eidenschik | ............... | 623/1.11 |
| 6,823,576 B2 | 11/2004 | Austin | ............... | 29/516 |
| 7,308,748 B2 * | 12/2007 | Kokish | ............... | 29/516 |
| 2002/0035774 A1 * | 3/2002 | Austin | ............... | 29/516 |
| 2003/0135970 A1 | 7/2003 | Thornton | ............... | 29/270 |
| 2003/0192164 A1 | 10/2003 | Austin | ............... | 29/505 |
| 2005/0033404 A1 | 2/2005 | Eidenschink | ............... | 709/224 |

OTHER PUBLICATIONS

U.S. Appl. No. 10/826,035, filed Apr. 16, 2004, Perreault.
U.S. Appl. No. 10/790,941, filed Mar. 1, 2004, Miller et al.
U.S. Appl. No. 10/748,444, filed Dec. 30, 2003, McCullagh.
U.S. Appl. No. 10/767,985, filed Jan. 29, 2004, Edin et al.
U.S. Appl. No. 10/788,088, filed Feb. 26, 2004, Weber et al.

* cited by examiner

*Primary Examiner*—Dana Ross
*Assistant Examiner*—Debra M Sullivan
(74) *Attorney, Agent, or Firm*—Crompton, Seager & Tufte, LLC.

(57) ABSTRACT

A system for reducing the diameter of a stent comprises a stent contracting assembly. The assembly comprises a plurality of blades, which define a diameter reduction chamber. The chamber has an open diameter configuration and a closed diameter configuration. The plurality of blades comprises active blades and floating blades, wherein each active blade is engaged to an actuation mechanism. The actuation mechanism is constructed and arranged to move each active blade from the open diameter configuration to the closed diameter configuration. Each floating blade is moved from the open diameter configuration to the closed diameter configuration only as a result of the movement of the active blades.

11 Claims, 11 Drawing Sheets

STENT CRIMPING MECHANISMS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to stents, stent loading, stent contracting and stent delivery systems and their respective methods of use. Some embodiments of the invention are more specifically directed to stent loading and crimping systems and their methods of use.

2. Description of Related Art

A stent is a generally tubular device that is used to support a bodily lumen. A stent is typically delivered to a desired bodily location via a catheter. Often the stent is loaded onto a portion of the catheter, such as a balloon or other region of the catheter shaft. In some stent delivery systems the stent is crimped to the catheter in order to minimize the profile of the stent on the catheter and to prevent undesired movement of the stent relative to the catheter shaft.

A number of techniques for loading and contracting a stent to a catheter shaft or balloon are used. One such technique utilizes a crimping head having an iris to constrict the diameter of the stent by moving a plurality of crimping fingers radially inward against the stent. Such an iris based crimping head is described in U.S. Pat. No. 6,629,350, the entire content of which is incorporated herein by reference. While such iris type mechanisms have demonstrated successful results in crimping both balloon expandable stents and self-expandable stents, it is known that in some cases, particularly involving some types of self-expanding stents, the stent can become caught or snagged within the gap(s) between the iris fingers. As a result, the stent and/or the iris fingers may be damaged. This reduces the life of the fingers and necessitates changing the iris fingers more often.

It would be desirable to provide an iris type crimping head having reduced or no gaps between the fingers.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is particularly concerned with the crimping and otherwise reducing size of stents, including bare or coated stents of any configuration or expansion type, including balloon expandable stents, self-expanding stents, hybrid expandable stents, etc. For the purpose of this disclosure, it is understood that the term 'stent' includes stents, stent-grafts, grafts and vena cava filters and other implantable medical devices for luminal support and/or treatment. It is also understood that the term 'crimping' refers to a reduction in size or profile of a stent and 'crimper' refers to devices for accomplishing such reduction in size or profile of a stent.

The present invention is embodied in a variety of forms. In some embodiments the invention is directed to stent reducing and/or loading-mechanisms such as stent crimpers and associated reducing and loading tools. In at least one embodiment a crimper comprises an iris chamber or other contractible and expandable opening defined by a plurality of moveable contacting members or fingers. The iris chamber may be adjusted between an open diameter and a closed diameter.

In at least one embodiment each of the fingers comprises at least two components including a finger or blade and a movement element. The movement element comprises a housing defining a hollow chamber. Extending from the hollow chamber through the housing wall are a plurality of dowel pins which are engaged to the blade. The dowel pins are configured to be moveable into and out of the hollow chamber of the housing, but the housing wall is configured to prevent or minimize any side to side or lateral movement of the dowel pins relative to the housing. One or more biasing members are contained within the hollow chamber and act to control the longitudinal movement of the blade relative to the housing.

In at least one embodiment one or more of the dowels extend into the hollow chamber of the housing and are engaged to one or more of the biasing members.

In at least one embodiment the biasing members are constructed and arranged to bias the dowel pins into the hollow chamber and/or out of the hollow chamber. In some embodiments different biasing members are configured to bias the dowel pins in different directions.

In at least one embodiment the biasing members are positioned off center relative to the dowel pins.

In at least one embodiment, biasing members are absent from one or more of the movement elements.

In at least one embodiment the biasing members are substituted with an electromagnetic drive mechanism.

In at least one embodiment the iris defined by the blades is has an expanded or opened diameter of at least 15 mm.

In at least one embodiment the iris is defined by a plurality of blades, wherein every other blade of the iris or crimping head is operatively engaged to a drive cam. Upon rotation of the drive cam the engaged blades are moved to contract or expand the iris opening depending on the direction of the drive cam's rotation. In some embodiments between each blade engaged to the drive cam is a blade which is not engaged to the drive cam. The unengaged or "floating" blades are passively actuated as a result of the actuation of the engaged or "active" blades adjacent thereto.

In at least one embodiment the movement element of each floating blade comprises a biasing member, which biases the floating blade toward the center of the iris opening independent of any cam actuation.

In some embodiments, the invention is directed to a crimper having a plurality of blades each of which have a contacting edge which is curved. The curved contacting edges substantially defining the iris opening.

The curvature of each blade trailing edge is defined such that, the path followed by the previous blade's tip when the mechanism operates, maintains constant contact along the trailing edge of the blade next to it. Maintaining constant contact minimizes the possibility of pinching or damaging the stent or the stent coating. The curved nature of the blades allows the crimping head to utilize a lesser number of blades than a more traditional design, which inherently provides a reduced number of blade "gaps" and thus, reduces the possibility of the stent adversely interacting with such gaps.

In at least one embodiment the crimper has 15 blades or less.

In at least one embodiment the crimper has 12 blades or less.

In at least one embodiment the crimper is comprised of 8 blades or less.

These and other embodiments which characterize the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings-in-which.

DETAILED DESCRIPTION OF THE INVENTION

Figure 1:
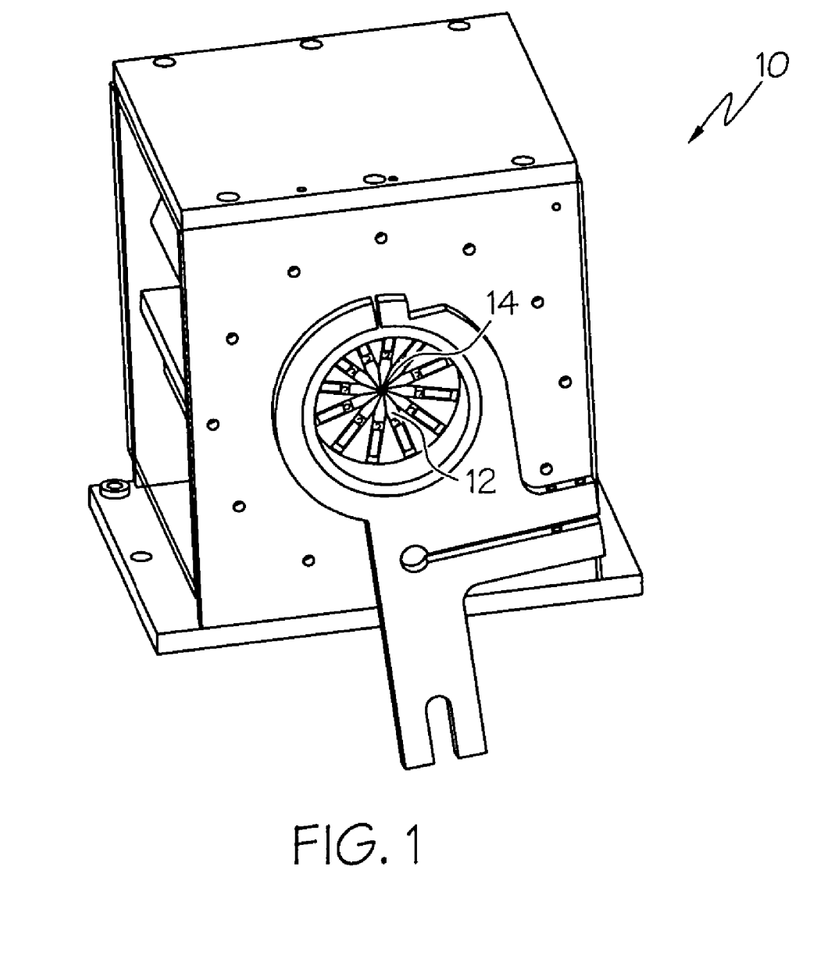
FIG. 1 is a front perspective view of an embodiment of the invention comprising a stent crimper.

As indicated above, the present invention is embodied in a variety of forms. In at least one embodiment, such as for example in the embodiment depicted in FIG. 1, the invention is directed to a radial stent reducing assembly or crimper 10.

In the embodiment shown, crimper 10 is provided with a plurality of stent reducing members or blades 12 which define a stent reduction chamber or iris opening 14 into which a stent or other medical device (not shown) may be positioned in order to reduce the stent from an unreduced diameter state. Unlike many prior stent crimping devices, the crimper 10 in the embodiment shown in FIGS. 1-7 is constructed and arranged to provide minimal to no spacing between the adjacent blades 12, or at least between portions of the blade that are in close proximity to the stent during the crimping process, such as is sown in FIGS. 4-6.

Figure 2:
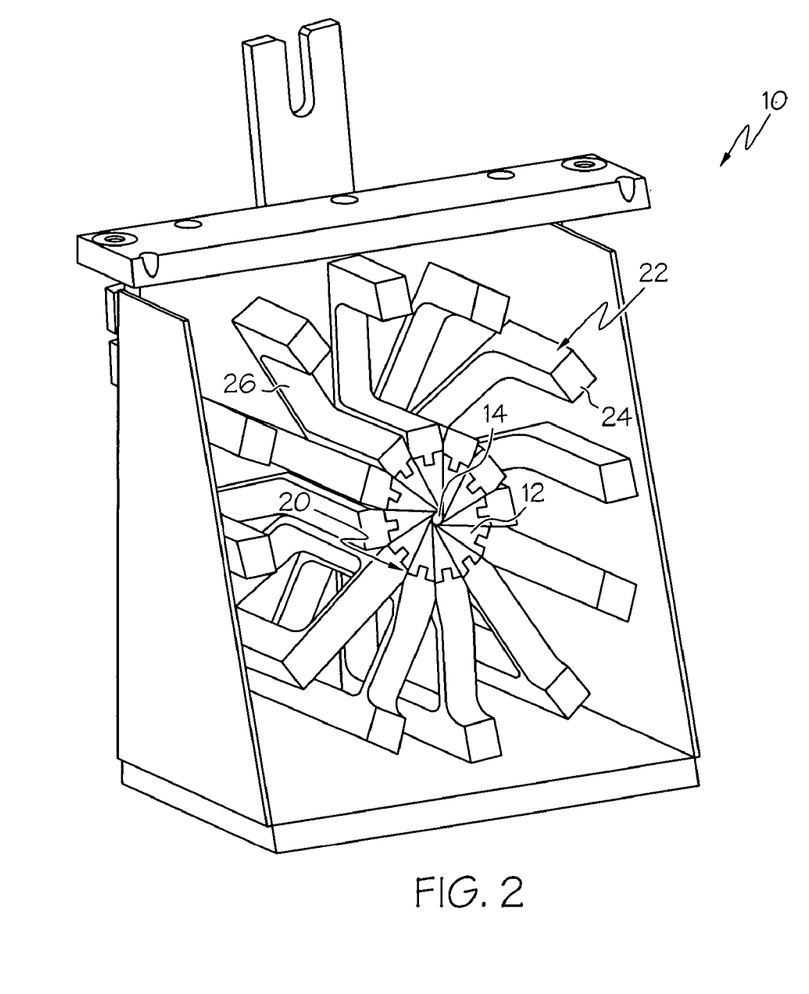
FIG. 2 is a detailed cut-away perspective view of the embodiment shown in FIG. 1.

As is shown in FIG. 2, the components of the crimper 10, include actuation elements or fingers 20 which may be considered to have two components. The first component of each finger 20, which is configured to contact or otherwise act upon the stent is the aforementioned blade 12. The second component of each finger 20 is a movement element 22. In the embodiment shown, each movement element 22 comprises a frame or housing 24, which defines a space or chamber 26. As is shown in FIGS. 2-6, the movement element 22 of a given finger 20 is operatively engaged to the corresponding blade 12.

Figure 3:
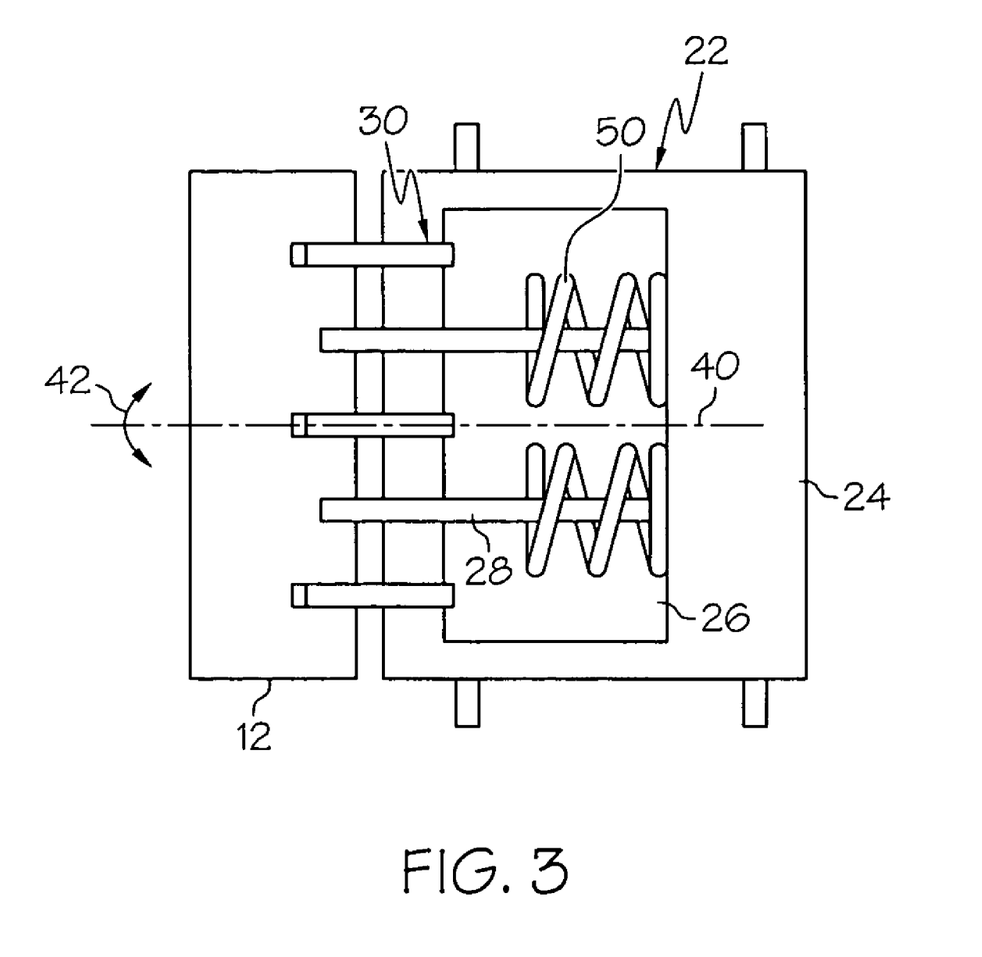
FIG. 3 is a side view of a movement element and blade from the crimper shown in FIGS. 1-2.
Figure 6:
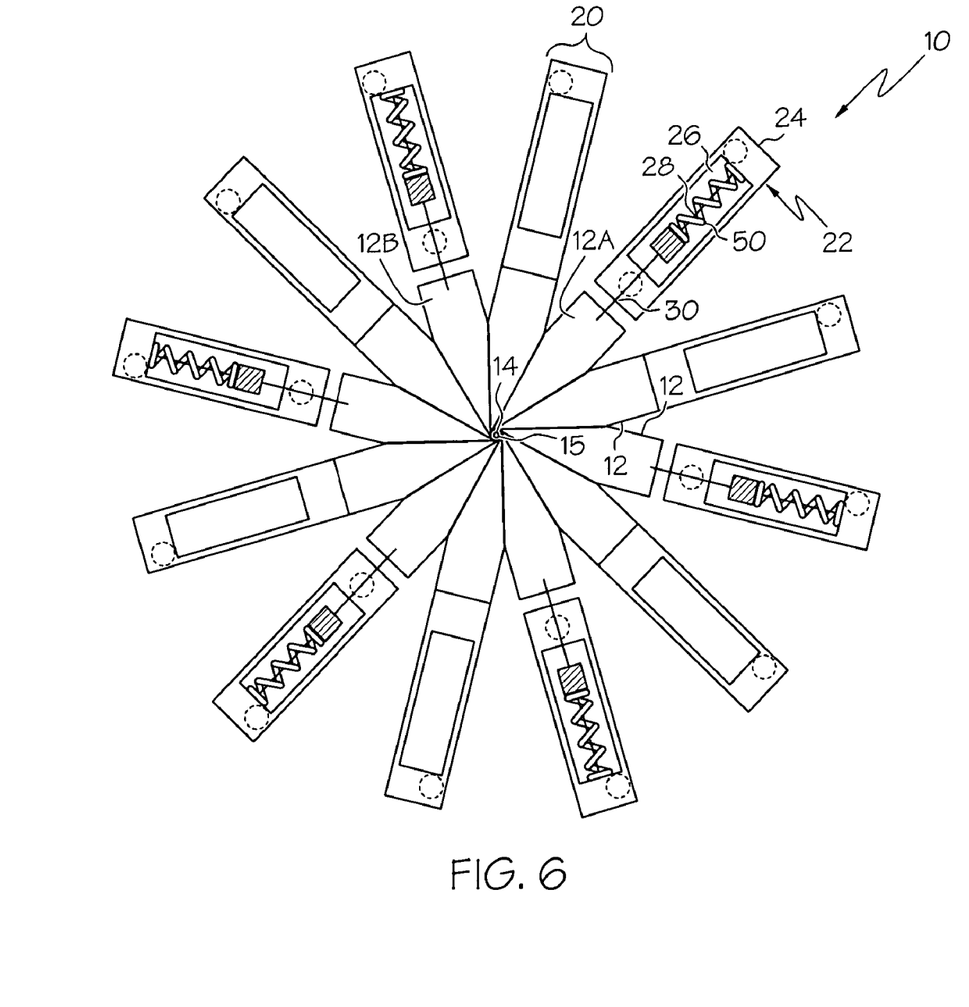

In at least one embodiment, an example of which is shown in FIG. 3, all of the movement elements or any number thereof can comprise a plurality of dowel pins 28 which extend through one or more openings 30 of the housing 24 to engage the blade 12. The number of dowel pins 28 may vary depending on the length of the crimping head and the stent to be crimped. Desirably, there is a very close tolerance between the size and shape of the openings 30 relative to the dowel pins 28. As a result, the dowel pins are provided with a single axis of movement, indicated by line 40, relative to the housing 24. Movement of the dowel pins into and out of the housing chamber 26 is as linear as possible, so that lateral or side-to-side movement, illustrated by arrows 42 is minimized or eliminated. By minimizing the lateral movement of the blades 12 allows the blades to move relative to one another with effectively no gaps between adjacent blade tips 16, particularly when the iris opening 14 is in the closed configuration, such as is shown in FIG. 6.

Figure 4:
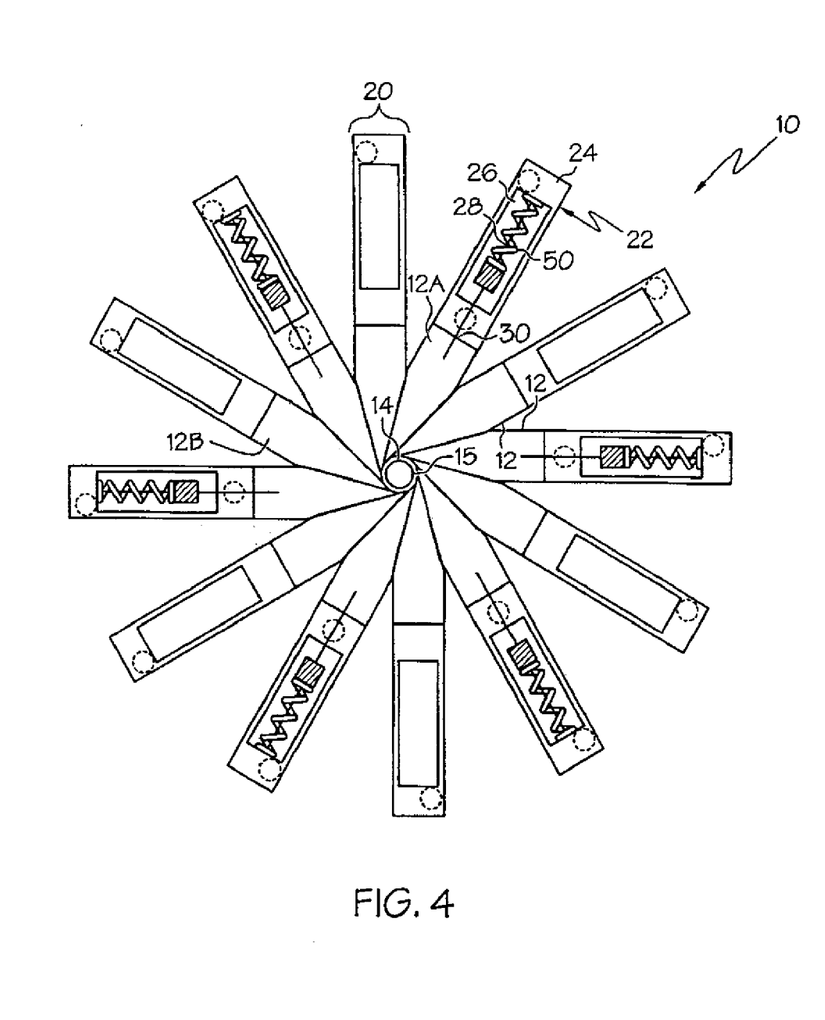
FIGS. 4-6 are a series of transverse cross-sectional views of the movement elements and blades of the embodiment shown in FIG. 2 shown during the crimping process.

As mentioned above, one or more of the dowel pins 28 are moveable relative to the housing 24. When the dowel pins are moved outward from the housing chamber 26, the blade 12, engaged to the dowel pins 28, is likewise moved in a direction away from the housing 24. When a plurality of the fingers 20 are configured in this manner the iris opening 14 transitioned from the open configuration such as is shown in FIG. 4 to the closed configuration shown in FIG. 6, transitioning through a partially open configuration illustrated in FIG. 5. As the iris opening 14 is closed, a stent 15 positioned therein is reduced from a first or un-crimped diameter to a second crimped or reduced diameter.

The iris opening 14 may have a range of openings from about 15 mm in the open configuration to about 1 mm in the closed configuration, however if desired the opening 14 may be completely closed.

In the various embodiments of the invention blade movement can be controlled by any desired actuation mechanism. In the example shown in FIGS. 3-6, where a finger 20 is equipped with actuatable dowel pins 28, the dowel pins are actuatable by force applied to the pins by one or more biasing members 50. The biasing members 50 are engaged to one or more of the dowel pins 28 within the housing chamber 26. The biasing members 50 may be any type of biasing mechanism such as one or more springs, levers, cams, pneumatics, etc., which bias the dowel pins 28 relative to the housing 24. In at least one embodiment the dowel pins 28 and biasing members 50 comprise an electromagnetic drive mechanism.

Figure 5:
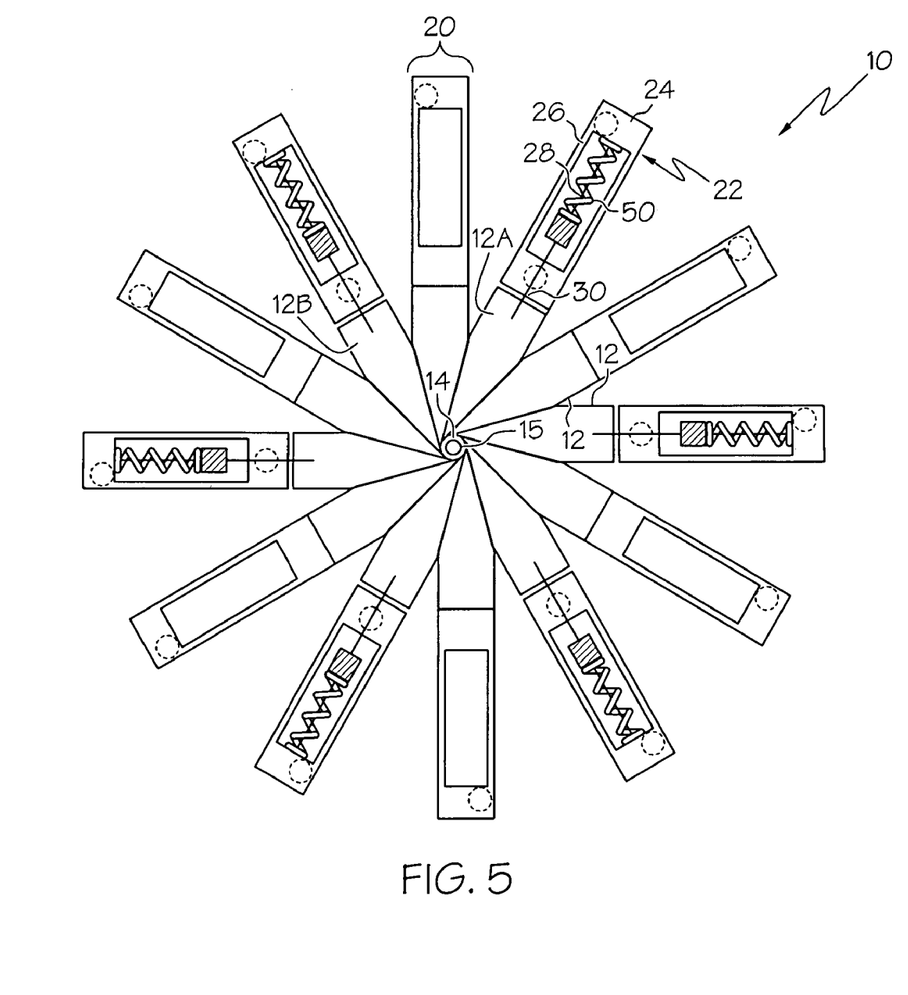

As is shown in the embodiment depicted in FIGS. 4-6, not all of the fingers 20 are equipped with dowel pins 28 which are actuatable by biasing members 50. Those fingers 20 which do not include biasing members 50 to actuate the blade 12, are in effect "floating" in the crimping head relative to those blades which are "active" or actuatable by the biasing members 50. An exemplary active blade is represented at 12a and an adjacent floating blade is indicated at 12b in FIGS. 4-6. Floating blades 12b will typically be fixedly engaged to the movement element, however in some embodiments one or more floating blades may be moveable relative to the movement elements but not actively actuated thereby.

When the active blades 12a of the crimper are actuated to close the iris opening 14 in the manner previously described, the shape and movement of the active blades 12a will cause the active blades 12a to frictionally engage the adjacent floating blades 12b. The interaction of the active blades 12a and the floating blades 12b further ensures the minimization of gaps between the blade tips 16 as the iris opening 14 is closed.

Figure 7:
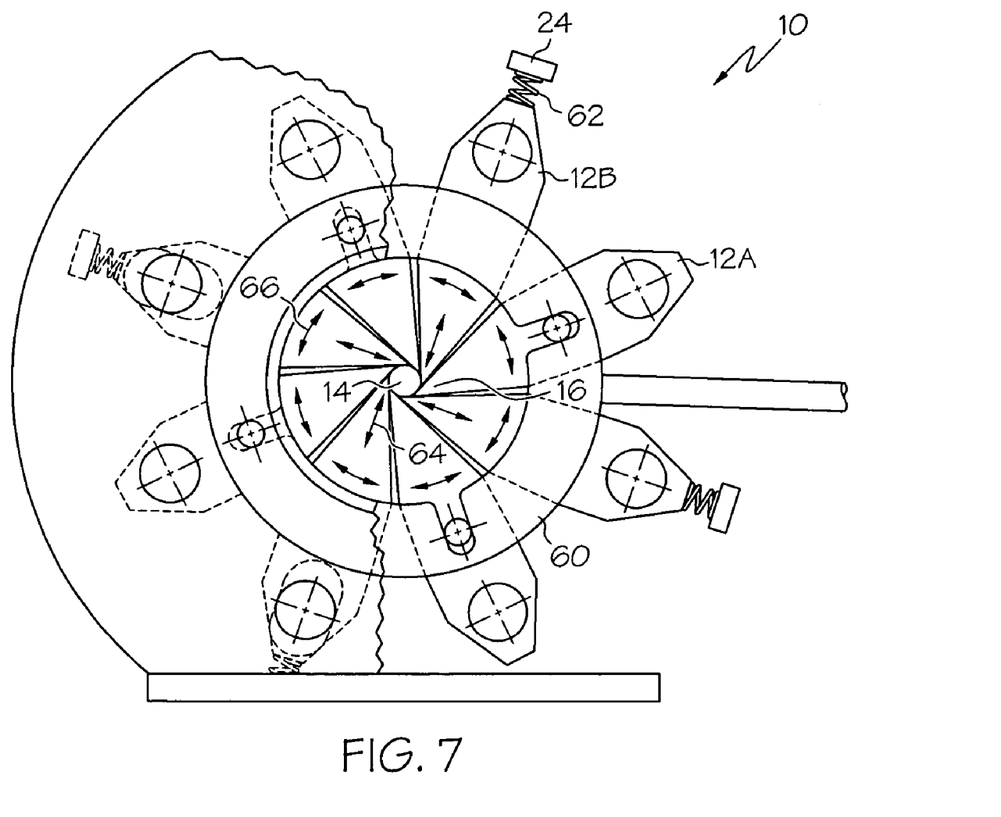
FIG. 7 is a cross-sectional view of an embodiment of the invention.
Figure 8:
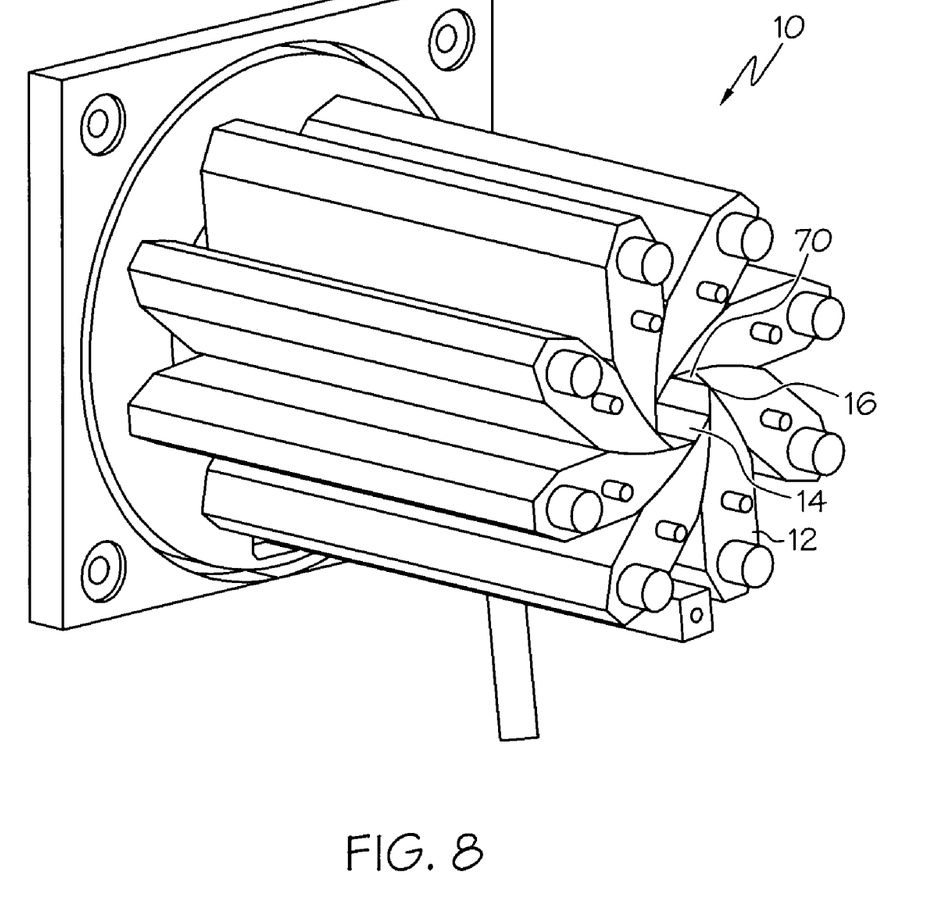
FIG. 8 is a perspective view of an embodiment of the invention wherein the blades of the crimper have curved contacting edges.

In at least one embodiment, an example of which is shown in FIG. 7, the crimper 10 comprises an iris opening 14 defined by a plurality of cam driven blades 12. In the embodiment shown, active blades 12a are operatively engaged to a rotating cam 60 such that when the cam is rotated the active blades 12a are drawn inward to close the iris opening 14. Positioned between each active blade 12a is a floating blade 12b. In the present embodiment the floating blades 12b are not operatively engaged to the cam 60, and passively move as a result of their interaction with the active blades 12a.

In at least one embodiment each of the floating blades 12b are mechanically constrained by a spring element 62 or other energy storing mechanism. The spring element 62 is engaged to a housing 24 and are configured to provide the blade 12b with one or more degrees of freedom, as desired. Though the floating blades 12b are not actuated by the rotation of the cam 60, the spring element 62 of each blade 12b allows the blade 12b to move both longitudinally, as indicated by arrows 64, and laterally, as indicated by arrows 66, when acted upon by the adjacent active blades 12a. Such freedom of motion allows the entire assembly of blades 12 to provide an iris opening 14 that is essentially free of potentially detrimental gaps between the tips 16 of the blades 12.

In some embodiments of the invention, an example of which is shown in FIGS. 8-11, the blades 12 of the crimper 10 each include an engagement surface or edge 70 which has a curved shape. The curved shape of each edge 70 substantially defines the iris opening 14.

As is shown in FIGS. 8-11, the curved nature of the blades 12 allows the crimper 10 to provide a substantially circular iris opening 14 with fewer blades than a more traditional crimping head. Typically a crimping head requires 15, 12, or even more blades to define the iris, whereas the present configuration shown, allows for as few as 8 blades to be used. In some embodiments the crimper 10 is comprised of less than 8 blades. By reducing the number of blades 12 present in the crimper 10 the number of potentially detrimental gaps between the blades is also reduced. If a more perfectly circular iris opening 14 is desired, the crimper 10 may be configured to include a greater number of blades 12 than that which is shown in the present figures. The greater the number of blades 12 present, the more perfectly circular the iris opening 14 may be configured to be.

Figure 9:
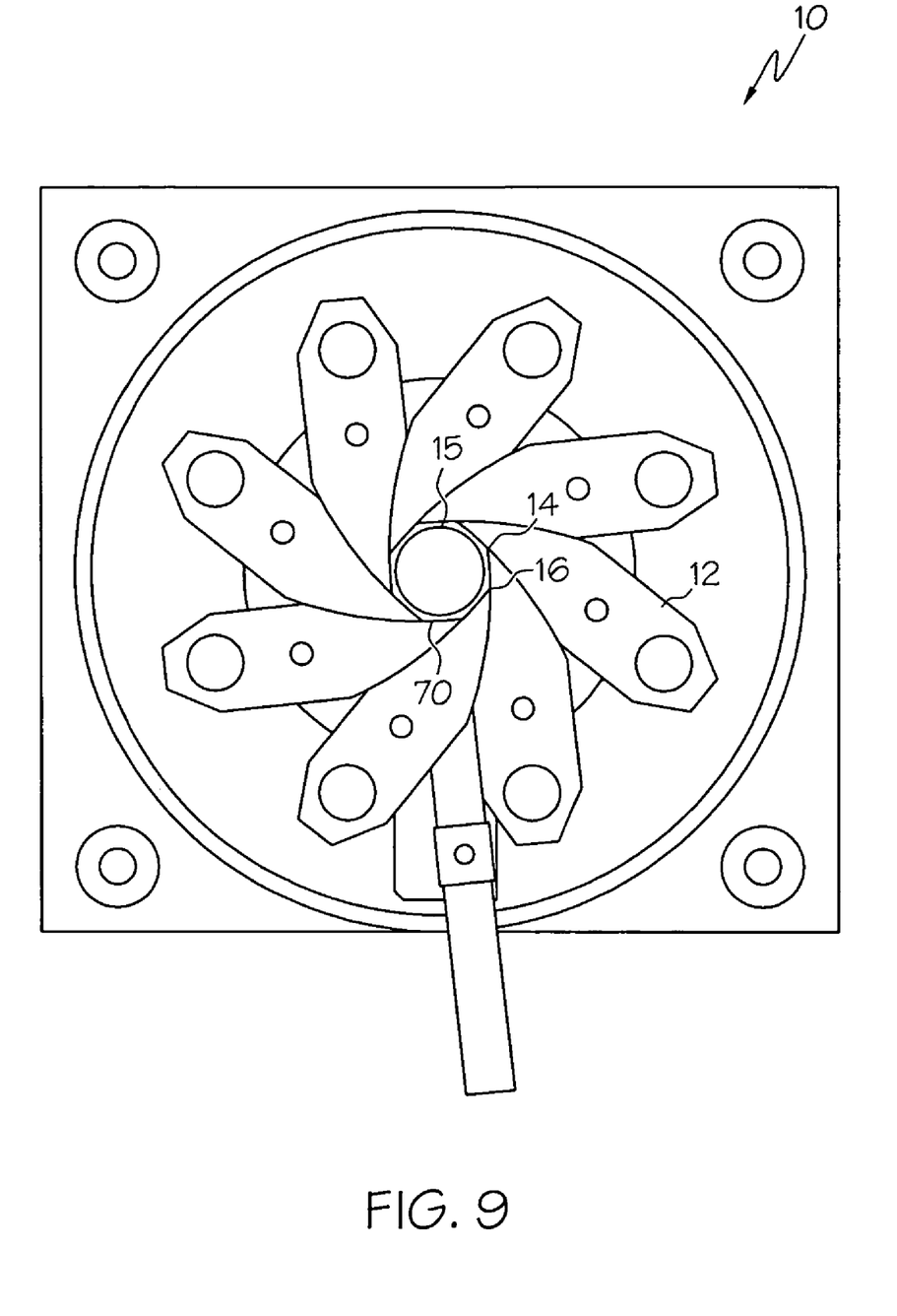
FIG. 9 is a front view of the embodiment shown in FIG. 8, wherein the iris opening of the crimper is shown in the open position.
Figure 10:
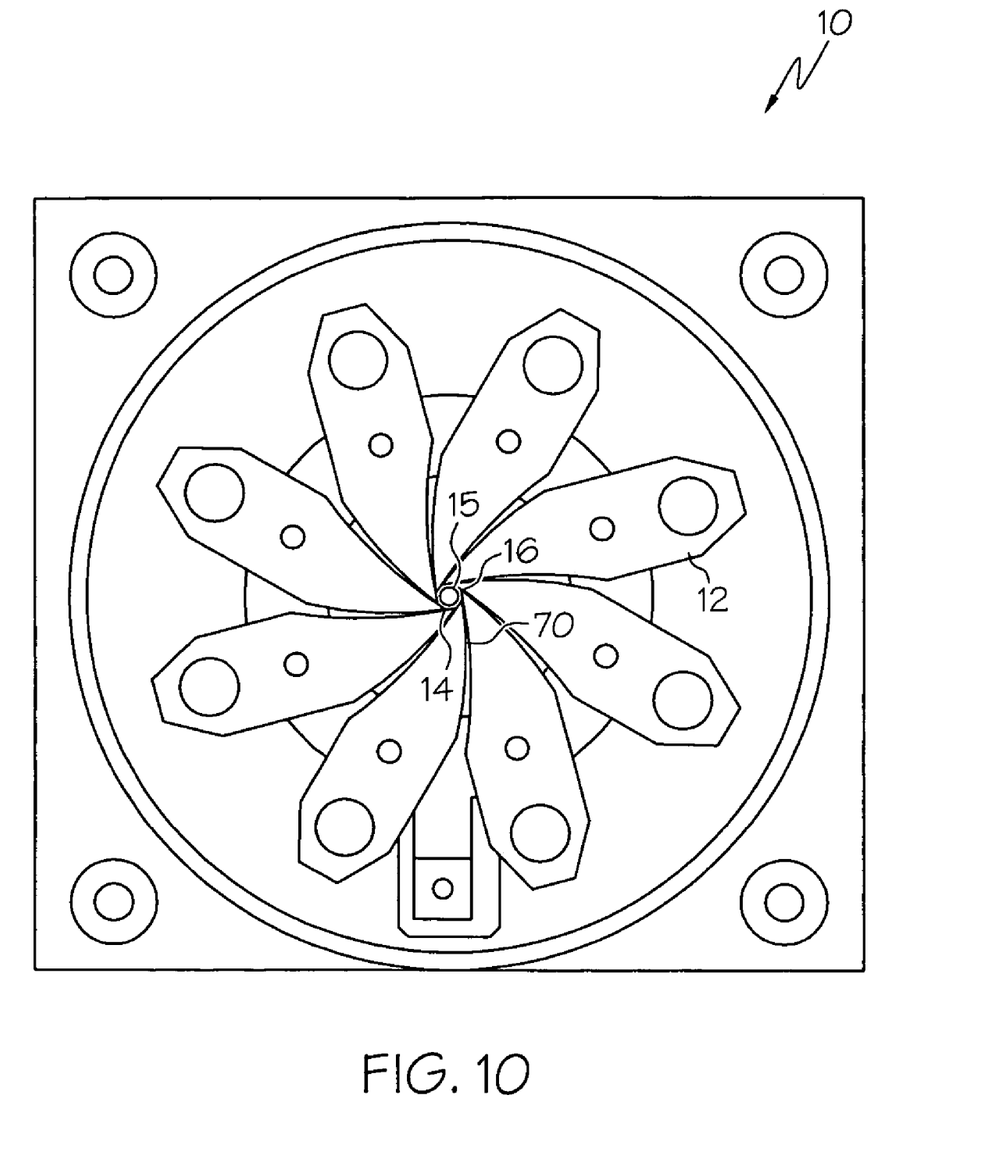
FIG. 10 is a front view of the embodiment shown in FIG. 9, wherein the iris opening of the crimper is shown partially opened or closed.
Figure 11:
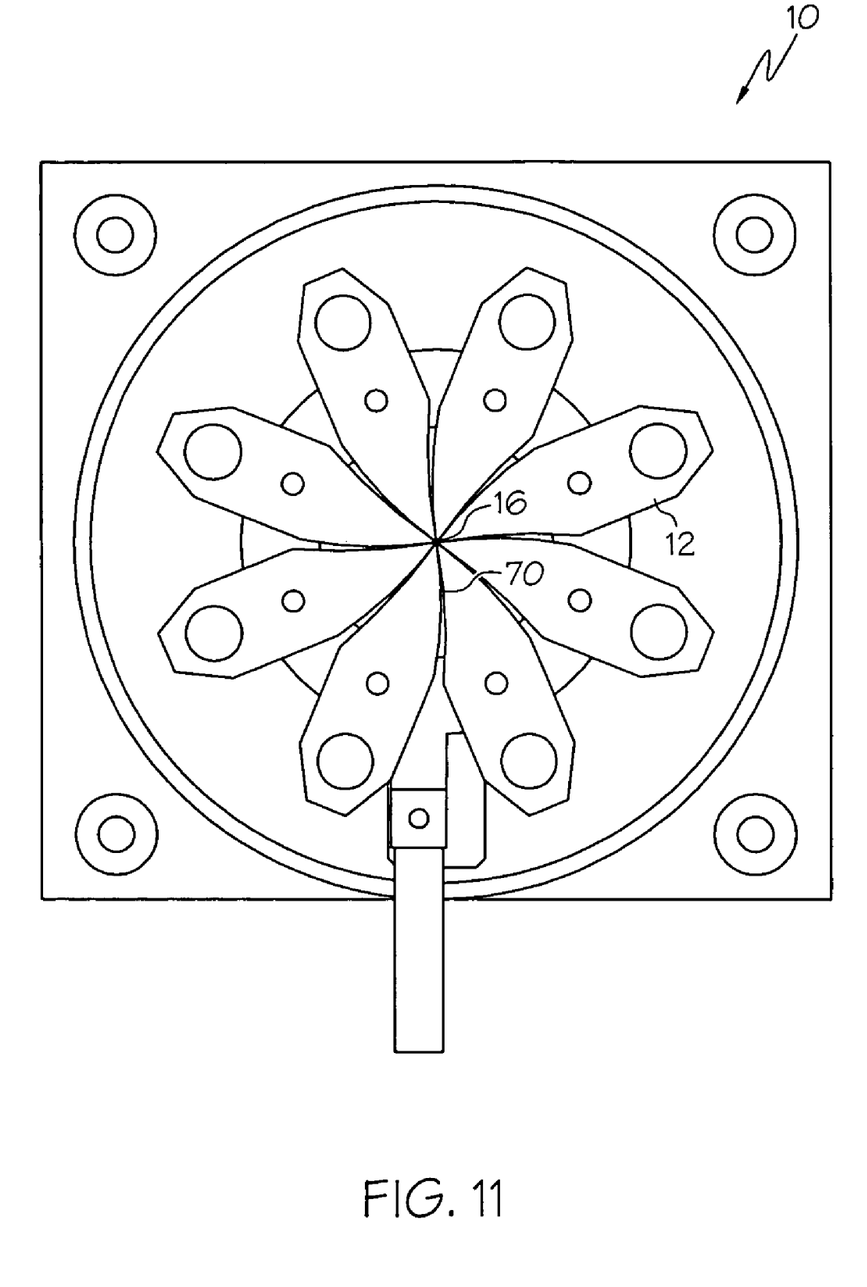
FIG. 11 is a front view of the embodiment shown in FIG. 10, wherein the iris opening of the crimper is shown in the closed position.

The curvature of each edge 70 is characterized such that, the path followed by the previous (adjacent) blade's tip 16 maintains constant contact with the edge of the blade adjacent thereto during the closing of the iris opening 14, such as is shown in FIGS. 9-11. Maintaining constant contact minimizes the possibility of pinching or damaging the stent 15 or the stent coating.

It should be noted that the various blade configurations and components (as well as other elements) shown and described herein may be exchanged and substituted within and between the various crimpers shown in FIGS. 1-11.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A system for reducing the diameter of a stent comprising:
a stent contracting assembly, the stent contracting assembly comprising a plurality of fingers, the plurality of contracting fingers defining a diameter reduction chamber, the chamber having an open diameter configuration and a closed diameter configuration, the contracting assembly constructed and arranged to receive a stent into and through the chamber, wherein when the chamber is in the open diameter configuration the stent has a first diameter and when the chamber is in the closed diameter configuration the stent has a second diameter, the second diameter being less than the first diameter;
wherein each finger includes a blade, wherein one or more of the blades are active blades and one or more of the blades are floating blades;
wherein each finger having an active blade also includes a movement element, the active blade being actuatable relative to the movement element by an actuation mechanism engaged to the active blade, the actuation mechanism constructed and arranged to move each active blade relative to the movement element such that the plurality of fingers move from the open diameter configuration to the closed diameter configuration, each floating blade not having an actuation mechanism;
each floating blade cooperating with the active blades during movement the plurality of fingers from the open diameter configuration to the closed diameter configuration.

2. The system of claim 1 wherein in at least the closed diameter configuration the plurality of fingers are immediately adjacent to one another.

3. The system of claim 1 wherein each floating blade is positioned between a pair of active blades.

4. The system of claim 1 wherein the actuation mechanism is a rotatable cam.

5. The system of claim 1 wherein each of the plurality of blades is at least partially curved.

6. The system of claim 1, wherein each finger having a floating blade also includes a movement element.

7. The system of claim 6, wherein the floating blade is moveable relative to the movement element.

8. The system of claim 6, wherein the floating blade is fixedly engaged to the movement element.

9. A system for reducing the diameter of a stent comprising:
a stent contracting assembly, the stent contracting assembly comprising a plurality of blades, the plurality of contracting blades defining a diameter reduction chamber, the chamber having an open diameter configuration and a closed diameter configuration, the contracting assembly constructed and arranged to receive a stein into and through the chamber, wherein when the chamber is in the open diameter configuration the stent has a first diameter and when the chamber is in the closed diameter configuration the stent has a second diameter, the second diameter being less than the first diameter;
the plurality of blades comprises active blades and floating blades, each active blade being engaged to an actuation mechanism, the actuation mechanism constructed and arranged to move each active blade from the open diameter configuration to the closed diameter configuration, each floating blade not having an actuation mechanism; each floating blade being movable from the open diameter configuration to the closed diameter configuration; and
a plurality of movement elements, each of the plurality of blades being operatively engaged to one of the movement elements, each movement element comprising a housing and at least one dowel pin, the housing defining a chamber and at least one opening in communication with the chamber, the at least one dowel pin engaged to one of the plurality of blades, the at least one dowel pin moveably positioned within the at least one opening and extending from the contracting blade to the chamber.

10. The system of claim 9 wherein motion of the at least one dowel pin is limited by the configuration of the at least one opening to minimize lateral movement of the dowel pin relative thereto.

11. The system of claim 9 wherein the actuation mechanism comprises at least one biasing member, each biasing member being engaged to the at least one dowel pin within the chamber.

* * * * *

UNITED STATES PATENT AND TRADEMARK OFFICE
CERTIFICATE OF CORRECTION

PATENT NO.         : 7,748,248 B2                                   Page 1 of 1
APPLICATION NO.    : 11/087411
DATED              : July 6, 2010
INVENTOR(S)        : Gabriel Sobrino Serrano et al.

It is certified that error appears in the above-identified patent and that said Letters Patent is hereby corrected as shown below:

Column 7
Line 8 delete "stein", and insert therefor -- stent --.

Signed and Sealed this

Seventh Day of September, 2010

David J. Kappos
*Director of the United States Patent and Trademark Office*